(12) United States Patent
Ishii et al.

(10) Patent No.: US 6,218,569 B1
(45) Date of Patent: Apr. 17, 2001

(54) POLYMERIZABLE ALICYCLIC ESTERS AND PROCESS PRODUCING THE SAME

(75) Inventors: Yasutaka Ishii, Takatsuki; Keizo Inoue, Himeji, both of (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/600,717

(22) PCT Filed: Nov. 15, 1999

(86) PCT No.: PCT/JP99/06374

§ 371 Date: Jul. 20, 2000

§ 102(e) Date: Jul. 20, 2000

(87) PCT Pub. No.: WO00/31017

PCT Pub. Date: Jun. 2, 2000

(30) Foreign Application Priority Data

Nov. 20, 1998 (JP) .................................................. 10-331686

(51) Int. Cl.$^7$ .................................................. C07C 69/52
(52) U.S. Cl. .................................................. 560/220
(58) Field of Search ............................................. 560/220

(56) References Cited

FOREIGN PATENT DOCUMENTS

| | | | |
|---|---|---|---|
| 0878738 | * 11/1998 | (EP) | . |
| 63-33350 | 2/1988 | (JP) | . |
| 338548A | 2/1991 | (JP) | . |
| 200745A3 | 9/1991 | (JP) | . |
| 11-35522 | 5/1999 | (JP) | . |
| WO 9961404 | * 12/1999 | (JP) | . |
| 11-335327 | 12/1999 | (JP) | . |
| 9961404 | 12/1999 | (WO) | . |

* cited by examiner

*Primary Examiner*—Ralph Gitomer
*Assistant Examiner*—D Khare
(74) *Attorney, Agent, or Firm*—Birch, Stewart, Kolasch & Birch, LLP

(57) ABSTRACT

The invented polymerizable alicyclic esters are shown by the following formula (1) or (2):

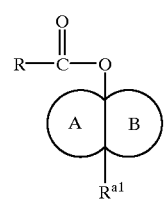

(1)

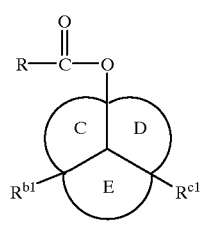

(2)

wherein each of ring A, ring B, ring C, ring D, and ring E is a non-aromatic carbon ring, R is a polymerizable unsaturated group, and each of $R^{a1}$, $R^{b1}$, and $R^{c1}$ is, identical to or different from one another, a hydrogen atom, a hydroxyl group which may be protected by a protective group, or an $RCO_2$ group, where R has the same meaning as defined above. Each of the ring A, ring B, ring C, ring D, and ring E is, for example, a cyclopentane ring, a cyclohexane ring, or a bridged ring. R includes, for example, a vinyl group, an isopropenyl group, or an aryl group.

6 Claims, No Drawings

POLYMERIZABLE ALICYCLIC ESTERS AND PROCESS PRODUCING THE SAME

This application is the national phase under 35 U.S.C. § 371 of PCT International Application No. PCT/JP99/06374 which has an International filing date of Nov. 15, 1999, which designated the United States of America.

TECHNICAL FIELD

The present invention relates to polymerizable alicyclic esters which are useful as monomers for photosensitive resins and other functional polymers, and to a process for producing the esters.

BACKGROUND ART

Alicyclic compounds each having a polymerizable unsaturated group are used as monomers for resist resins and other functional polymers, and have received attention in recent years.

However, no knowledge has been obtained about alicyclic ester compounds each having a polycyclic carbon ring composed of two or three non-aromatic carbon rings each having two carbon atoms in common and having a polymerizable unsaturated carboxylic acyloxy group bonded to a carbon atom at the junction position between two rings, and about processes for producing the ester compounds.

DISCLOSURE OF INVENTION

Accordingly, an object of the invention is to provide a novel alicyclic ester compound having a polycyclic carbon ring composed of two or three non-aromatic carbon rings each having two carbon atoms in common and having a polymerizable unsaturated carboxylic acyloxy group bonded to a carbon atom at the junction position between two rings, and a process for producing the ester compound.

The present inventors made intensive investigations to achieve the above object, and found that when an alicyclic alcohol having a polycyclic carbon ring composed of two or three non-aromatic carbon rings each possessing two carbon atoms in common and having a hydroxyl group on a carbon atom at the junction position between two rings is allowed to react with a polymerizable unsaturated carboxylic acid in the presence of a specific catalyst, an esterification reaction smoothly proceeds to yield a corresponding novel alicyclic ester, even though the hydroxyl group is bonded to a sterically crowded position. The invention, has been accomplished based on these findings.

Specifically, the invention provides a polymerizable alicyclic ester shown by the following formula (1) or (2):

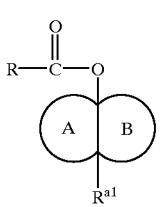

(1)

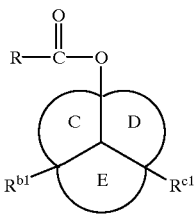

(2)

wherein each of ring A, ring B, ring C, ring D, and ring E is a non-aromatic carbon ring, R is a polymerizable unsaturated group, and each of $R^{a1}$, $R^{b1}$ and $R^{c1}$ is, identical to or different from one another, a hydrogen atom, a hydroxyl group which may be protected by a protective group, or an $RCO_2$ group, where R has the same meaning as defined above.

The invention provides, in another aspect, a process for producing a polymerizable alicyclic ester. The process includes the step of allowing an alicyclic alcohol shown by the following formula (3) or (4):

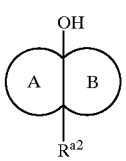

(3)

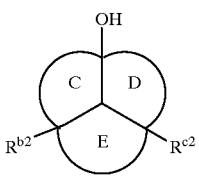

(4)

wherein each of ring A, ring B, ring C, ring D, and ring E is a non-aromatic carbon ring, and each of $R^{a2}$, $R^{b2}$, and $R^{c2}$ is, identical to or different from one another, a hydrogen atom or a hydroxyl group which may be protected by a protective group, to react with an unsaturated carboxylic acid shown by the following formula (5):

$$RCO_2H \quad (5)$$

wherein R is a polymerizable unsaturated group, or a reactive derivative thereof in the presence of a catalyst composed of a compound of Group 3 element of the Periodic Table of Elements to yield the ester of the formula (1) or (2).

In the present description, "acryl" and "methacryl" may be abbreviated to "(meth)acryl", and "acryloyl" and "methacryloyl" may be abbreviated to "(meth)acryloyl".

BEST MODE FOR CARRYING OUT THE INVENTION

In the invented polymerizable alicyclic esters, each of the ring A, ring B, ring C, ring D, and ring E is a non-aromatic carbon ring. Such non-aromatic carbon rings include monocyclic or polycyclic rings (e.g., bridged rings) each having about 3 to 20 carbon atoms. The carbon rings may have a double bond as far as the rings are non-aromatic. If the carbon rings are polycyclic rings, the carbon rings may each have an additional aromatic ring, as far as a ring joined to the adjacent ring (the ring A, ring B, ring C, ring D or ring E) is a non-aromatic carbon ring.

Typical examples of the non-aromatic carbon rings include cyclopropane ring, cyclobutane ring, cyclopentane ring, cyclopentene ring, cyclohexane ring, cyclohexene ring, cycloheptane ring, cyclooctane ring, cyclodecane ring, cyclododecane ring, cyclopentadecane ring, and other monocyclic rings; perhydroindene ring, decalin ring, norbornane ring, norbornene ring, bicyclo[2.2.2]octane ring, and other bridged rings. Among these rings, cyclopentane ring, cyclohexane ring, and bridged rings are preferred.

The non-aromatic carbon rings may have a substituent. Such substituents include halogen atoms such as fluorine, chlorine, bromine, or iodine atom; alkyl groups such as methyl, ethyl, isopropyl, and other $C_1$–$C_6$ alkyl groups, especially $C_1$–$C_4$ alkyl groups; cycloalkyl groups; aryl groups such as phenyl group and naphthyl group; hydroxyl group; alkoxy groups such as methoxy, ethoxy, isopropoxy, and other $C_1$–$C_6$ alkoxy groups, especially $C_1$–$C_4$ alkoxy groups; acyloxy groups such as acetyloxy, propionyloxy, (meth)acryloyloxy, and other $C_2$–$C_6$ aliphatic acyloxy groups, especially $C_2$–$C_4$ aliphatic acyloxy groups; carboxyl group; alkoxycarbonyl groups such as methoxycarbonyl, ethoxycarbonyl, propoxycarbonyl, and other $C_1$–$C_6$ alkoxycarbonyl groups, especially $C_1$–$C_4$ alkoxycarbonyl groups; substituted or unsubstituted carbamoyl groups such as carbamoyl group; methylcarbamoyl, dimethylcarbamoyl, diethylcarbamoyl, and other mono- or di-$C_1$–$C_4$ alkyl-substituted carbamoyl groups; acyl groups such as acetyl, propionyl, and other $C_2$–$C_6$ aliphatic acyl groups, especially $C_2$–$C_4$ aliphatic acyl groups; oxo group; substituted or unsubstituted amino groups such as amino group, methylamino, ethylamino, propyl amino, dimethylamino, diethylamino, and other mono- or di-$C_1$–$C_6$ alkyl-substituted amino groups, especially mono- or di-$C_1$–$C_4$ alkyl-substituted amino groups; cyano group; and nitro group. The hydroxyl group, carboxyl group, and amino group may be protected by a conventional protective group.

In the formula (1), polycyclic carbon rings formed by the ring A and the ring B include, but are not limited to, perhydroindene ring, decalin ring, perhydrofluorene ring, perhydroanthracene ring, perhydrophenanthrene ring, and tricyclo[5.2.1.0$^{2,6}$]decane ring. In the formula (2), polycyclic carbon rings formed by the ring C, the ring D, and the ring E include, but are not limited to, perhydroacenaphthene ring and perhydrophenalene ring.

The polymerizable unsaturated groups in the substituent R include hydrocarbon groups each having a polymerizable double bond such as vinyl group, isopropenyl group, allyl group, allylmethyl group, and other allyl-$C_1$–$C_4$ alkyl groups, 2-methyl-2-propenyl group and other α-alkyl-substituted vinyl-$C_1$–$C_4$ alkyl groups; and hydrocarbon groups each having a polymerizable triple bond such as ethynyl group, 2-propynyl group and other ethynyl-$C_1$–$C_4$ alkyl groups. Preferred polymerizable unsaturated groups each have an α,β-ethylenically unsaturatedbond. Such preferred polymerizable unsaturated groups include vinyl group, isopropenyl group, and allyl group, of which vinyl group or Isopropenyl group is typically preferred.

Each of the substituents $R^{a1}$, $R^{b1}$ and $R^{c1}$ is, identical to or different from one another, a hydrogen atom, a hydroxyl group which may be protected by a protective group, or an $RCO_2$ group, where R has the same meaning as defined above. The protective groups for hydroxyl group may be conventional protective groups Such protective groups include, but are not limited to, alkyl groups such as methyl and t-butyl groups; alkenyl groups such as allyl group; cycloalkyl groups such as cyclohexyl group; aryl groups such as 2,4-dinitrophenyl group; aralkyl groups such as benzyl, 2,6-dichlorobenzyl, 3-bromobenzyl, 2-nitrobenzyl, and triphenylmethyl groups; substituted methyl groups such as methoxymethyl, methylthiomethyl, benzyloxymethyl, t-butoxymethyl, 2-methoxyethoxymethyl, 2,2,2-trichloroethoxymethyl, bis(2-chloroethoxy)methyl, and 2-(trimethylsilyl)ethoxymethyl groups; substituted ethyl groups such as 1-ethoxyethyl, 1-methyl-1-methoxyethyl, 1-isopropoxyethyl, and 2,2,2-trichloroethyl groups; tetrahydropyranyl group; tetrahydrofuranyl group; saturated aliphatic acyl groups such as formyl, acetyl, propionyl, butyryl, isobutyryl, valeryl, pivaloyl, and other $C_2$–$C_6$ saturated aliphatic acyl groups; aromatic acyl groups such as benzoyl and naphthoyl groups; acetoacetyl group; alkoxycarbonyl groups such as methoxycarbonyl, ethoxycarbonyl, and t-butoxycarbonyl groups; aralkyloxycarbonyl groups such as benzyloxycarbonyl group and p-methoxybenzyloxycarbonyl group; dialkylphosphinothioyl groups such as dimethylphosphinothioyl group; diarylphosphinothioyl groups such as diphenylphosphinothicyl group; substituted silyl groups such as trimethylsilyl, t-butyldimethylsilyl, tribenzylsilyl, and triphenylsilyl groups; substituted or unsubstituted carbamoyl groups such as carbamoyl, methylcarbamoyl, and phenylcarbamoyl groups.

The substituent $R^{a1}$ is preferably a hydroxyl group which may be protected by a protective group, or an $RCO_2$ group. At least one of the substituents $R^{b1}$ and $R^{c1}$ is preferably a hydroxyl group which may be protected by a protective group, or an $RCO_2$ group.

Preferred polymerizable alicyclic esters include (i) compounds where $R^{a1}$ in the formula (1) is a hydroxyl group which may be protected by a protective group, or an $RCO_2$ group; (ii) compounds each having at least one hydroxyl group which may be protected by a protective group or an $RCO_2$ group in at least one ring (except for the junction position between the ring A and ring B) of the ring A and the ring B in the formula (1) (iii) compounds where at least one of the substituents $R^{b1}$ and $R^{c1}$ in the formula (2) is a hydroxyl group which may be protected by a protective group, or an $RCO_2$ group; and (iv) compounds each having at least one hydroxyl group which may be protected by a protective group or an $RCO_2$ group in at least one ring (except for the junction position of each ring) of the ring C, the ring D, and the ring E in the formula (2).

Typical examples of the polymerizable alicyclic esters include, but are not limited to, 3a-(meth)acryloyloxyperhydroindene, 3a-[(meth)acryloyloxy]-7a-hydroxyperhydroindene, 3a,7a-bis[(meth)acryloyloxy]perhydroindene, 4a-(meth)acryloyloxydecalin, 4a-(meth)acryloyloxy-8a-hydroxydecalin, 4a,8a-bis[(meth)acryloyloxy]decalin, 4a-(meth)acryloyloxyperhydrofluorene, 4a-[(meth)acryloyloxy]-9a-hydroxyperhydrofluorene, 4a,9a-bis[(meth)acryloyloxy]perhydrofluorene, 4a-(meth)acryloyloxyperhydroanthracene, 4a-(meth)acryloyloxy-9a-hydroxyperhydroanthracene, 4a,9a-bis[(meth)acryloyloxy]perhydroanthracene, 10a-(meth)acryloyloxyperhydrophenanthrene, 10a-(meth)acryloyloxy-4a-hydroxyperhydrophenanthrene, 4a,10a-bis [(meth)acryloyloxy]perhydrophenanthrene, 2-(meth)acryloyloxytricyclo[5.2.1.0$^{2,6}$]decane, 2-(meth)acryloyloxy-6-hydroxytricyclo[5.2.1.0$^{2,6}$]decane, 2-(meth)acryloyloxy-5-hydroxytricyclo[5.2.1.0$^{2,6}$]decane, 2,6-bis[(meth)acryloyloxy]tricyclo[5.2.1.0$^{2,6}$]decane, 2,5-bis[(meth)acryloyloxy]tricyclo[5.2.1.0$^{2,6}$]decane, 2a-(meth)acryloyloxyperhydroacenaphthene, 2a-(meth)acryloyloxy-8a-hydroxyperhydroacenaphthene, 2a,8a-bis[(meth)

acryloyloxy]perhydroacenaphthene, 3a-(meth)acryloyloxyperhydrophenalene, 3a-(meth)acryloyloxy-9a-hydroxyperhydrophenalene, and 3a,9a-bis[(meth)acryloyloxy]perhydrophenalene.

In the compounds of the formula (3) or formula (4) used as materials in the invented process, the ring A, ring B, ring C, ring D and ring E have the same meanings as defined above, and each of $R^{a2}$, $R^{b2}$, and $R^{c2}$ is, identical to or different from one another, a hydrogen atom or a hydroxyl group which may be protected by a protective group. Such protective groups for hydroxyl group include, for example, the aforementioned protective groups. The substituent $R^{a2}$ is preferably a hydroxyl group which may be protected by a protective group. At least one of the substituents $R^{b2}$ and $R^{c2}$ is preferably a hydroxyl group which may be protected by a protective group.

Typical examples of the alicyclic alcohols of the formula (3) or formula (4) include, but are not limited to, 3a-hydroxyperhydroindene, 3a,7a-dihydroxyperhydroindene, 4a-hydroxydecalin, 4a,8a-dihydroxydecalin, 4a-hydroxyperhydrofluorene, 4a,9a-dihydroxyperhydrofluorene, 4a-hydroxyperhydroanthracene, 4a,9a-dihydroxyperhydroanthracene, 10a-hydroxyperhydrophenanthrene, 4a,10a-dihydroxyperhydrophenanthrene, 2-hydroxytricyclo[5.2.1.0$^{2,6}$]decane, 2,6-dihydroxytricyclo[5.2.1.0$^{2,6}$]decane, 2,5-dihydroxytricyclo[5.2.1.0$^{2,6}$]decane, 2a-hydroxyperhydroacenaphthene, 2a,8a-dihydroxyperhydroacenaphthene, 3a-hydroxyperhydrophenalene, and 3a,9a-dihydroxyperhydrophenalene.

The alicyclic alcohols of the formula (3) or (4) can be prepared by, for example, oxidizing a compound of the following formula (6) or (7):

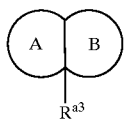

(6)

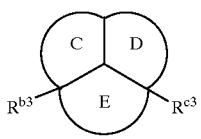

(7)

wherein each of $R^{a3}$, $R^{b3}$, and $R^{c3}$ is, identical to or different from one another, a hydrogen atom or a hydroxyl group which may be protected by a protective group, and ring A, ring B, ring C, ring D and ring E have the same meanings as defined above, with a molecular oxygen in the presence of an imide commound of the following formula (8):

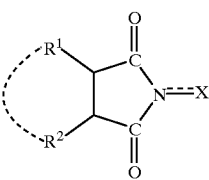

(8)

wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond or an aromatic or non-aromatic ring; X is an oxygen atom or a hydroxyl group, where one or two N-substituted cyclic imido groups indicated in the formula (8) may be further bonded to the aforementioned $R^1$, $R^2$ or to the double bond or aromatic or non-aromatic ring formed by $R^1$ and $R^2$, or in the presence of the imide compound and a metallic compound.

In the formulae (6) and (7), protective groups for hydroxyl group include, for example, the aforementioned protective groups.

Of the substituents $R^1$ and $R^2$ in the formula (8), the halogen atom includes iodine, bromine, chlorine, and fluorine atoms. The alkyl group includes, for example, methyl, ethyl isopropyl, and other alkyl groups each having about 1 to 10 carbon atoms. The aryl group includes, for example, phenyl and naphthyl groups, and the cycloalkyl group includes, for example, cyclopentyl and cyclohexyl groups. Illustrative alkoxy groups are methoxy, ethoxy, propoxy, and other alkoxy groups each having about 1 to 10 carbon atoms. Illustrative alkoxycarbonyl groups are methoxycarbonyl, ethoxycarbonyl, propoxycarbonyl, and other alkoxycarbonyl groups each having about 1 to 10 carbon atoms in the alkoxy moiety. The acyl group includes, for example, formyl, acetyl, propionyl, and other acyl groups each having about 1 to 6 carbon atoms.

The substituents $R^1$ and $R^2$ maybe identical to, or different from each other. The substituents $R^1$ and $R^2$ in the formula (8) may be combined to form a double bond, or an aromatic or non-aromatic ring. The preferred aromatic or non-aromatic ring is a 5- to 12-membered ring, and especially a 6- to 10-membered ring. The ring may be a heterocyclic ring or a condensed heterocyclic ring, but it is often a hydrocarbon ring. Such rings include, for example, non-aromalic alicyclic rings (e.g., cyclohexane ring and other cycloalkane rings which may have a substituent, cyclohexene ring and other cycloalkene rings whichmay have a substituent), non-aromatic bridged rings (e.g., 5-norbornene ring and other bridged hydrocarbon rings which may have a substituent), benzene ring, naphthalene ring and other aromatic rings (including condensed rings) which may have a substituent. The ring is composed of an aromatic ring in many cases.

In the formula (8), X represents an oxygen atom or a hydroxyl group, and the bond between the nitrogen atom N and X is a single bond or a double bond.

Illustrative preferred imide compounds include N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxychlorendimide, N-hydroxyhimimide, N-hydroxytrimellitimide, N,N'-dihydroxypyromellitimide, and N,N'-dihydroxynaphthalenetetracarboximide.

The imide compounds of the formula (8) can be prepared by a conventional imidation process (a process for the formation of an imide), such as a process including the steps of allowing a corresponding acid anhydride to react with hydroxylamine $NH_2OH$ for ring-opening of an acid anhydride group, and closing the ring to form an imide.

The imide compound can be used as being supported by a carrier or support. As such carriers, activated carbon, zeolite, silica, silica-alumina, bentonite, and other porous carries are often employed.

The amount of the imide compound can be selected in a wide range and is, for example, about 0.0001 to 1 mole, preferably about 0.001 to 0.5 mole, and more preferably about 0.01 to 0.4 mole, relative to 1 mole of the compound of the formula (6) or (7).

Metallic elements for constituting the metallic compounds are not critical and can be any of metallic elements of the Groups 1 to 15 of the Periodic Table of Elements. The term "metallic element" as used herein also includes boron, B. Examples of the metallic elements include, of the Periodic Table of Elements, Group 1 elements (e.g., Li, Na, K), Group 2 elements (e.g., Mg, Ca, Sr, Ba), Groups 3 elements (e.g., Sc, lanthanoid elements, actinoid elements), Group 4 elements (e.g., Ti, Zr, Hf), Group 5 elements (e.g., V), Group 6 elements (e.g., Cr, Mo, W), Group 7 elements (e.g., Mn), Group8 elements (e.g., Fe, Ru), Group 9 elements (e.g., Co, Rh), Group 10 elements (e.g., Ni, Pd, Pt), Group 11 elements (e.g., Cu), Group 12 elements (e.g., Zn), Groups 13 elements (e.g., B, Al, In), Group 14 elements (e.g., Sn, Pb), and Group 15 elements (e.g., Sb, Bi). Preferred metallic elements include transition metal elements (elements of Groups 3 to 12 of the Periodic Table of Elements). Among them, elements of the Groups 5 to 11, especially elements of Groups 6,7 and 9 of the Periodic Table of Elements are preferred, of which Mo, Co and Mn are typically preferred. The valence of the metallic element is not critical, and may be about 0 to 6 in many cases.

The metallic compounds include, but are not limited to, elementary substances, hydroxides, oxides (including complex oxides), halides (fluorides, chlorides, bromides, and iodides), salts of oxoacids (e.g., nirates, sulfates, phosphates, borates, and carbonates), oxoacids, isopolyacids, heteropolyacids, and other inorganic compounds of the aforementioned metallic elements; salts of organic acids (e.g., salts of acetic acid, propionic acid, hydrocyanic acid, naphthenic acid, and stearic acid), complexes, and other organic compounds of the metallic elements. Ligands for constituting the complexes include OH (hydroxo), alkoxy (e.g., methoxy, ethoxy, propoxy, and butoxy groups), acyl (e.g., acetyl, and propionyl), alkoxycarbonyl (e.g., methoxycarbonyl, and ethoxycarbonyl), acetylacetonato, cyclopentadienyl group, halogen atoms (e.g., chlorine and bromine atoms), CO, CN, oxygen atom, $H_2O$ (aquo), phosphines (e.g., triphenylphosphine and other triarylphosphines), and other phosphorus compounds, $NH_3$ (ammine), NO, $N_2O$ (nitro), $N_3O$ (nitrato), ethylenediamine, diethylenetriamine, pyridine, phenanthroline, and other nitrogen-containing compounds.

Concrete examples of the metallic compounds include, by taking cobalt compounds as example, cobalt hydroxide, cobalt oxide, cobalt chloride, cobalt bromide, cobalt nitrate, cobalt sulfate, cobalt phosphate, and other inorganic compounds; cobalt acetate, cobalt naphthenate, cobalt stearate, and other salts of organic acids; cobalt acetylacetonato, and other complexes, and other divalent or trivalent cobalt compounds. Illustrative vanadium compounds include vanadium hydroxide, vanadium oxide, vanadium chloride, vanadyl chloride, vanadium sulfate, vanadyl sulfate, sodiumvanadate, and other inorganic compounds; vanadium acetylacetonato, vanadyl acetylacetonato, and other complexes, and other vanadium compounds having a valence of 2 to 5. Examples of molybdenum compounds include molybdenum hydroxide, molybdenum oxide, molybdenum chloride, molybdenum bromide, molybdenum sulfide, molybdic acid or its salts, phosphomolybdic acid or its salts, silicomolybdic acid or its salts, and other inorganic compounds; molybdenum carbonyl, bis(acetylacetonato) dioxomolybdenum, chlorotricarbonyl($\eta$-cyclopentadienyl) molybdenum, dibromobis($\eta$-cyclopentadienylmolybdenum, and other complexes, and other molybdenum compounds having a valence of 0 to 6. Examples of compounds of the other metallic elements include compounds corresponding to the above-mentioned cobalt, vanadium or molybdenum compounds. Each of the metallic compounds can be used alone or in combination.

The proportion of the metallic compound is, for example, about 0.0001 to 0.7 mole, preferably about 0.001 to 0.5 mole, and more preferably about 0.002 to 0.1 mole, relative to 1 mole of the compound of the formula (6) or (7).

The molecular oxygen for use in the reaction includes, but is not limited to, pure oxygen, and oxygen diluted with an inert gas such as nitrogen, helium, argon or carbon dioxide. Air is advantageously used as the molecular oxygen from the view points of operating property and safety, as well as cost efficiency. The molecular oxygen is often used in excess moles relative to the compound of the formula (6) or (7).

The oxidation reaction is generally performed in an organic solvent. Such organic solvents include, but are not limited to, acetic acid, propionic acid, and other organic acids; acetonitrile, propionitrile, benzonitrile, and other nitriles; formamide, acetamide, dimethylformamide (DMF), dimethylacetamide, and other amides; hexane, octane, and other aliphatic hydrocarbons; chloroform, dichloromethane, dichloroethane, carbon tetrachloride, chlorobenzene, trifluoromethylbenzene, and other halogenated hydrocarbons; nitrobenzene, nitromethane, nitroethane, and other nitro compounds; ethyl acetate, butyl acetate, and other esters; and mixtures of these solvents. In may cases, acetic acid and other organic acids, acetonitrile, benzonitrile, and other nitriles, trifluorobenzene, and other halogenated hydrocarbons, ethyl acetate and other esters are used as the solvent.

The reaction temperature in the oxidation reaction is, for example, about 0° C. to 300° C., preferably about 20° C. to 200° C., and more preferably about 30° C. to 150° C. The reaction is generally performed at a temperature ranging from about 40° C. to 100° C. The reaction can be carried out at atmospheric pressure or under pressure. When the reaction is conducted under pressure, the pressure is usually about 1 to 100 atm (e.g. 1.5 to 80 atm), preferably about 2 to 70 atm. The reaction time can adequately be selected within an appropriate range of, for example, about 30 minutes to 48 hours according to the reaction temperature and pressure.

The oxidation reaction can be performed in a batch system, a semi-batch system, a continuous system or another conventional system, in the presence of, or under flow of, molecular oxygen. By appropriately selecting the reaction condition, when $R^{a3}$, $R^{b3}$ or $R^{c3}$ is a hydrogen atom, the hydrogen atom can be converted into a hydroxyl group, or a hydroxyl group can be introduced into a ring-constituting carbon atom other than that at the junction position between two rings.

After the completion of the reaction, reaction products can be easily separated and purified in a conventional technique.

Such techniques include, for example, filtration, concentration, distillation, extraction, crystallization, recrystallization, column chromatography and other separation means, and any combination of these separation means.

In the Invented process, polymerizable unsaturated groups shown by R in the formula (5) include those mentioned above. Unsaturated carboxylic acids of the formula (5) include, but are not limited to, compounds each having a polymerizable double bond [e.g., (meth)acrylic acid, crotonic acid, vinylacetic acid, allylacetic acid, and other monocarboxylic acids; maleic acid, fumaric acid, itaconic acid, and other polycarboxylic acids; monoalkyl esters of these polycarboxylic acids] and compounds each having a polymerizable triple bond (e.g., propiolic acid).

Reactive derivatives of these unsaturated carboxylic acids include acid anhydrides such as (meth)acrylic anhydride and maleic anhydride; and compounds each having a leaving group. Such leaving groups include, but are not limited to, halogen atoms, alkyl groups, alkenyl groups, alkynyl groups, aryl groups, cycloalkyl groups, and aralkyl groups.

Such reactive derivatives of carboxylic acids each having a leaving group include, but are not limited to, acid halides such as (meth)acrylic chloride and (meth)acrylic bromide; alkyl esters of carboxylic acids such as methyl (meth)acrylate, ethyl (meth)acrylate, propyl (meth)acrylate, butyl (meth)acrylate, isobutyl (meth)acrylate, t-butyl (meth) acrylate, and other $C_1$–$C_6$, alkyl esters of carboxylic acids, especially $C_1$–$C_4$ alkyl esters of carboxylic acids; alkenyl esters of carboxylic acids such as vinyl (meth)acrylate, allyl (meth)acrylate, 1-propenyl (meth)acrylate, isopropenyl (meth)acrylate, 1-butenyl (meth)acrylate, 2-butenyl (meth) acrylate, 3-butenyl (meth)acrylate, 2-pentenyl (meth) acrylate, and other $C_2$–$C_{10}$ alkenyl esters of carboxylic acid, especially $C_2$–$C_6$ alkenyl esters of carboxylic acids, typically $C_2$–$C_4$ alkenyl esters of carboxylic acids; alkynyl esters of carboxylic acids such as ethynyl (meth)acrylate, propynyl (meth)acrylate, and other $C_2$–$C_{10}$ alkynyl esters of carboxylic acids, especially $C_2$–$C_6$ alkynyl esters of carboxylic acids, typically $C_2$–$C_4$ alkynyl esters of carboxylic acids; aryl esters of carboxylic acids such as phenyl (meth)acrylate; cycloalkyl esters of carboxylic acids such as cyclohexyl (meth)acrylate, and other $C_3$–$C_{10}$ cycloalkyl esters of carboxylic acids; aralkyl esters of carboxylic acids such as benzyl (meth)acrylate, and other phenyl-$C_1$–$C_4$ alkyl esters of carboxylic acids.

Preferred reactive derivatives include carboxylic halides, $C_1$–$C_6$ alkyl esters of carboxylic acids (especially $C_1$–$C_4$ alkyl esters of carboxylic acids), $C_2$–$C_6$ alkenyl esters of carboxylic acids (typically $C_2$–$C_4$ alkenyl esters of carboxylic acids), and $C_1$–$C_6$ alkynyl esters of carboxylic acids (typically $C_2$–$C_4$ alkynyl esters of carboxylic acids). Especially, the use of carboxylic halides or $C_2$–$C_6$ alkenyl esters of carboxylic acids can yield the polymerizable aliphatic ester at a high selectively in a high yield through an exchange reaction of a leaving group, while suppressing additional polymerization and other side reactions.

According to the invented process, the formation of amine hydrochlorides or the like can be suppressed. In addition, when a $C_1$–$C_4$ alkyl ester of carboxylic acid or a $C_2$–$C_4$ alkenyl ester of carboxylic acid is used, no halogen component contaminates a target compound. Furthermore, a low boiling compound such as the above ester can be used as the reactant unsaturated carboxylic acid or a reactive derivative thereof, and a treatment after the reaction can be easily performed and the isolation yield can be markedly improved.

In the invention, to improve a reaction efficiency to thereby obtain the polymerizable alicyclic ester in a high yield, an alicyclic alcohol of the formula (3) or (4) is subjected to an esterification reaction (including a transesterification reaction and other leaving group exchange reactions) with the unsaturated carboxylic acid of the formula (5) or a reactive derivative thereof in the presence of a catalyst composed of a compound of Group 3 element of the Periodic Table of Elements.

In catalysts composed of compounds of Group 3 elements of the Periodic Table of Elements, such Group 3 elements of the Periodic Table of Elements include rare earth elements such as scandium, yttrium, and lanthanoid elements (lanthanum, cerium, praseodymium, neodymium, promethium, samarium, europium, gadolinium, terbium, dysprosium, holmium, erbium, thulium, ytterbium, and lutetium); and actinoid elements such as actinium.

Preferred Group 3 elements of the Periodic Table of Elements include rare earth elements such as scandium, yttrium, and lanthanoid elements (e.g., samarium, gadolinium, and ytterbium). Especially, samarium has a high catalytic activity.

In such compounds of Group 3 elements of the Periodic Table of Elements, the valence of the Group 3 element of the Periodic Table of Elements is not critical and is typically about 2 to 4, and frequently 2 or 3. The types of the compounds of Group 3 elements of the Periodic Table of Elements are not limited as far as the compounds have a catalytic activity, and include elementally metals, and inorganic compounds (e.g., halides, oxides, double oxides, phosphorus compounds, nitrogen compounds) or compounds with organic compounds (e.g., organic acids) or complexes. The compounds are often hydroxides or salts of oxygen acids, salts of organic acids, salts of inorganic acids, or halides, each containing the above elements, or coordination compounds (complexes) containing the metal elements. Such complexes may be metallocene compounds and other π complexes. The compounds of Group 3 elements of the Periodic Table of Elements may be complex metallic compounds with other metals. Each of these catalysts can be used alone or in combination.

By taking samarium compounds as example, the catalytic component will be illustrated in detail below. Naturally, compounds of other Group 3 elements of the Periodic Table of Elements corresponding to samarium compounds can be also effectively employed.

Hydroxides include, for example, samarium (II) hydroxide, and samarium(III) hydroxide. Metallic oxides include, for example, samarium(II) oxide and samarium(III) oxide.

Salts of organic acids include, but are not limited to, salts of organic acids such as organic carboxylic acids (e.g., formic acid, acetic acid, trichloroacetic acid, trifluoroacetic acid, propionic acid, butyric acid, valeric acid, naphthenic acid, stearic acid, and other monocarboxylic acids; oxalic acid, maleic acid, and other polycarboxylic acids), hydroxycarboxylic acids (e.g., glycolic acid, lactic acid, malic acid, tartaric acid, and citric acid), thiocyanic acid, and sulfonic acids (e.g., methanesulfonic acid, trichloromethanesulfonic acid, trifluoromethanesulfonic acid, ethanesulfonic acid, and other alkylsulfonic acids; benzenesulfonic acid, p-toluenesulfonic acid, and other arylsulfonic acids). Salts of inorganic acids include, but are not limited to, nitrates, sulfates, phosphates, carbonates, and perchlorates. Illustrative organic acid salts or inorganic acid salts include, but are not limited to, samarium(II) acetate, samarium(III) acetate, samarium (II) trichloroacetate, samarium(III) trichloroacetate, samarium(II) trifluoroacetate, samarium (III) trifluoroacetate, samarium(II) trifluoromethanesulfonate (i.e., samarium(II) triflate), samarium(III) trifluoromethanesulfonate (i.e., samarium(III) triflate), samarium (II) nitrate, samarium(II) sulfate, samarium(II) phosphate, and samarium(II) carbonate.

Halides include fluorides, chlorides, bromides and iodides, such as samarium(II) iodide, samarium(III) iodide, samarium(II) bromide, samarium(III) bromide, samarium (II) chloride, and samarium(III) chloride.

Ligands constituting complexes include, but are not limited to, OH (hydroxo), methoxy, ethoxy, propoxy, and butoxy, and other alkoxy groups, acetyl, propionyl, and other acyl groups, methoxycarbonyl (acetato), ethoxycarbonyl, and other alkoxycarbonyl groups, acetylacetonato, cyclopentadienyl, $C_1$–$C_4$ alkyl-substituted cyclopentadienyl groups (e.g., pentamethylcyclopentadienyl, and other $C_1$–$C_2$ alkyl-substituted cyclopentadienyl groups), dicyclopentadienyl, $C_1$–$C_4$ alkyl-substituted dicyclopentadienyl groups (e.g., pentamethyldicyclopentadienyl, and other $C_1$–$C_2$ alkyl-substituted dicyclopentadienyl groups), chlorine, bromine, and other halogen atoms, CO, CN, oxygen atom, $H_2O$ (aquo), phosphines (e.g., triphenylphosphine, and other triarylphosphines), and other phosphorus compounds, $NH_3$ (ammine), NO, $NO_2$ (nitro), $NO_3$ (nitrato), ethylenediamine, diethylenetriamine, pyridine, phenanthroline, and other nitrogen-containing compounds. One or more identical or different ligands may be coordinated in the complexes or complex salts.

Typical samarium complexes include, for example, bisacetylacetonatosamarium(II),
trisacetylacetonatosamarium(III),
biscyclopentadienylsamarium(II),
triscyclopentadienylsamarium(III),
bispentamethylcyclopentadienylsamarium(II),
trispentamethylcyclopentadienylsamarium(III), and bis($\eta^5$-pentamethylcyclopentadienyl)samarium(II).

The catalyst composed of a compound of Group 3 element of the Periodic Table of Elements may be homogenous or heterogenous. The catalyst may be a solid catalyst comprising the catalytic component of a Group 3 element of the Periodic Table of Elements supported by a carrier. As the carrier, activated carbon, zeolite, silica, silica-alumina, bentonite, and other porous carriers are often employed. The proportion of the catalytic component, the compound of Group 3 element of the Periodic Table of Elements, in such a solid catalyst is about 0.1 to 50 parts by weight, preferably about 0.5 to 30 parts by weight, and more preferably 1 to 20 parts by weight, relative to 100 parts by weight of the carrier.

The amount of the catalyst composed of a compound of Group 3 element of the Periodic Table of Elements can be selected within a wide range, and is, for example, about 0.1 to 100% by mole, preferably about 0.5 to 50% by mole, and more preferably about 1 to25% by mole (e.g., about 5to 20% by mole), relative to the alicyclic alcohol.

The esterification reaction is advantageously performed in the presence of anoxime. The oxime can be either an aldoxime or a ketoxime. Such oximes include, for example, 2-hexanone oxime, and other aliphatic oximes, cyclohexanone oxime, and other alicyclic oximes, acetophenone oxime, benzophenone oxime, benzyl dioxime and other aromatic oximes.

The amount of the oxime can be appropriately selected within a wide range of, for example, about 0.1 to 100% by mole, preferably about 1 to 50% by mole, and more preferably about 5 to 40% by mole (e.g., about 5 to 30% by mole), relative to the alicyclic alcohol.

The ratio of the unsaturated carboxylic acid of the formula (5) or a reactive derivative thereof relative to the alicyclic alcohol of the formula (3) or (4) can be freely selected within a range not adversely affecting the production efficiency of the polymerizable alicyclic ester, and is, for example, about 0.5 to 5 equivalents, preferably about 0.8 equivalent or more (e.g., about 0.8 to 5 equivalents), and typically about 1 equivalent or more (e.g., about 1 to 3 equivalents, and especially about 1 to 1.5 equivalent) relative to 1 equivalent of the alicyclic alcohol. The esterification reaction is an equilibrium reaction, and the more the amount of the unsaturated carboxylic acid of the formula (5) or a reactive derivative thereof is, the more advantageously the reaction proceeds. However, the aforementioned catalyst has a markedly high catalytic activity, and the use of the catalyst does not require large excess of the unsaturated carboxylic acid or a reactive derivative thereof. When the alicyclic alcohol of the formula (3) or (4) has two or more hydroxyl groups, a monoester, a diester, or the like can be obtained in a high yield by appropriately selecting the amount of the unsaturated carboxylic acid of the formula (5) or a reactive derivative thereof.

The invented process, where the heat of reaction is low, can smoothly proceed the reaction and can yield the target compound in a high yield even if the amount of a solvent is small.

The esterification reaction can be performed in the presence of, or in the absence of an inert solvent. Such reaction solvents include, but are not limited to, hexane, octane, and other aliphatic hydrocarbons; cyclohexane, and other alicyclic hydrocarbons; benzene, toluene, xylene, and other aromatic hydrocarbons; acetone, methyl ethyl ketone, methyl isobutyl ketone, and other ketones; dioxane, diethyl ether, diisopropyl ether, tetrahydrofuran, and other ethers; dimethylformamide, dimethylacetamide, N-methylpyrrolidone, acetonitrile, benzonitrile, and other non-protonic polar solvents; and mixtures of these solvents. The unsaturated carboxylic acid or a reactive derivative thereof can be employed as a reaction solvent.

Of the alicyclic alcohols, compounds each having a plurality of hydroxyl groups have a high hydrophilicity, and is liable to form a heterogenous reaction system when a generally-employed solvent for esterification reaction (toluene and other hydrophobic solvents) is used. Accordingly, when an alicyclic alcohol having a high hydrophilicity is employed, preferred solvents include hydrophilic solvents, or mixtures of hydrophilic solvents with hydrophobic solvents (aliphatic, alicyclic, or aromatic hydrocarbons). Such hydrophilic solvents include acetone, methyl ethyl ketone, and other ketones; dioxane, diethyl ether, tetrahydrofuran, and other ethers; and non-protonic polar solvents.

The reaction is an equilibrium reaction, and eliminated components or other components that adversely affect the reaction should be advantageously immediately removed out of the reaction system, in order to enhance the reaction. To remove the eliminated component, it is advantageous to use a high boiling solvent (e.g., an organic solvent having a boiling point of about 50° C. to 120° C., typically about 60° C. to 115° C.) or an azeotropic solvent (e.g., the aforementioned hydrocarbons).

The reaction temperature in the esterification reaction can be selected within a range of, for example, about 0° C. to 150° C., and preferably about 25° C. to 120° C. The use of the catalyst composed of a compound of Group 3 element of the periodic Table of Elements can yield the polymerizable alicyclic ester in a high yield even under mild conditions. In this case, the reaction temperature may be, for example, about 10° C. to 100° C., and preferably about 20° C. to 80°

C. Especially, the use of the alkenyl ester of organic carboxylic acid or the like as the unsaturated carboxylic acid or a reactive derivative thereof can smoothly proceed the reaction even under mild conditions of about 20° C. to 50° C. The reaction can be conducted under atmospheric pressure, under reduced pressure, or under pressure, in a batch system, a semi-batch system, a continuous system, or another conventional system.

After the completion of the reaction, the polymerizable alicyclic ester as a reaction product can be easily separated and purified in a conventional manner such as filtration, concentration, distillation, extraction, crystallization, recrystallization, column chromatography, and other separation means, or a combination of these separation means.

The invented polymerizable alicyclic ester can be prepared by, in addition to the above process, (A) a process of allowing the alicyclic alcohol of the formula (3) or (4) to react with the unsaturated carboxylic acid of the formula (5) in an appropriate solvent in the presence of an acid (e.g., hydrochloric acid, sulfuric acid, p-toluenesulfonic acid, or a cation exchange resin) at a temperature of, for example, about 0° C. to 150° C., while removing a by-produced water according to necessity, or (B) a process of allowing the alicyclic alcohol of the formula (3) or (4) to react with a reactive derivative (e.g., an acid halide, or an acid anhydride) of the unsaturated carboxylic acid of the formula (5) in an appropriate solvent, where necessary in the presence of a base such as triethylamine or pyridine.

The invented polymerizable alicyclic esters are polymerizable by action of heat or light in the presence of, or in the absence of a polymerization initiator (or a photopolymerization initiator). Polymers of the polymerizable alicyclic esters are satisfactory in optical properties, mechanical properties, thermal characteristics and electric characteristics. The polymerizable alicyclic esters can be therefore used in various applications. Such applications include, for example, optically functional materials such as optical fibers and coating compositions thereof, optic devices, optical lenses, holograms, optical disks, contact lenses, and other optical materials, coating compositions for organic glasses, conductive polymers, photographic sensitive materials, fluorescent materials; coating compositions (including paints); adhesives; and improvers or modifiers for polymers.

The invention can provide a novel alicyclic ester compound having a polycyclic carbon ring composed of two or three non-aromatic carbon rings each having two carbon atoms in common and having a polymerizable unsaturated carboxylic acyloxy group bonded to a carbon atom at the junction position between two rings.

The invented process can produce the alicyclic ester in a high yield with a high selectivity.

The present invention will now be described in more detail with reference to several examples below, which are not intended to limit the scope of the invention.

PREPARATION EXAMPLE 1

A mixture of 1.38 g (10 mmol) of cis-decalin, 0.16 g (1 mmol) of N-hydroxyphthalimide, 0.007 g (0.05 mmol) of $MoO_3$, and 10 ml of benzonitrile was stirred at 75° C. in an oxygen atmosphere (1 atm) for 6 hours. A gas chromatographic analysis of products in a reaction mixture revealed that cis-decalin was converted at a rate of 85% into 4a-hydroxy-cis-decalin in a yield of 61%, and into 4a,8a-dihydroxy-cis-decalin in a yield of 18%.

PREPARATION EXAMPLE 2

The procedure of Example 1 was repeated, except that 1.92 g (10 mmol) of cis-syn-cis-perhydroanthracene was used instead of cis-decalin. As a result, cis-syn-cis-perhydroanthracene was converted at a rate of 58% into 4a-hydroxy-cis-syn-cis-perhydroanthracene in a yield of 30%, and into 4a,9a-dihydroxy-cis-syn-cis-perhydroanthracene in a yield of 16%.

PREPARATION EXAMPLE 3

A mixture of 1.36 g (10 mmol) of exotricyclo[$5.2.1.0^{2,6}$] decane, 0.16 g (1 mmol) of N-hydroxyphthalimide, 0.007 g (0.05 mmol) of $MoO_3$, and 10 ml of acetic acid was stirred at 65° C. in an oxygen atmosphere (1 atm) for 6 hours. A gas chromatographic analysis of products in a reaction mixture revealed that exotricyclo[$5.2.1.0^{2,6}$]decane was converted at a rate of 43% into 2-hydroxyexotricyclo[$5.2.1.0^{2,6}$]decane in a yield of 31%, and into 2,6-dihydroxyexotricyclo[$5.2.1.0^{2,6}$]decane in a yield of 10%.

EXAMPLE 1

A mixed solution containing 1 mmol of 4a,8a-dihydroxy-cis-decalin, 0.1 mmol of samarium iodide ($SmI_2$), and 2.2 mmol of isopropenyl acrylate in 2 ml of dioxane was stirred at 50° C. for 6 hours. A gas chromatographic analysis of a reaction mixture revealed that 4a,8a-bisacryloyloxy-cis-decalin of the following formula was formed in a yield of 78%.

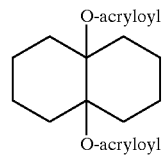

[Spectrum Data of 4a,8a-Bisacryloyloxy-cis-decalin]
$^1$H-NMR (CDCl$_3$) δ: 6.4 (d, 2H), 6.1 (dd, 2H), 5.8 (dd, 2H) 2.1–1.1 (m, 16H)

MS m/e: 279 (M$^+$)

EXAMPLE 2

The procedure of Example 1 was repeated, except that the amount of isopropenyl acrylate was chanced to 1 mmol. As a result, 4a-acryloyloxy-8a-hydroxy-cis-decalin of the following formula was formed in a yield of 47%.

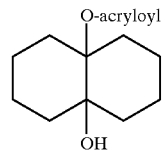

[Spectrum Data of 4a-Acryloyloxy-8 a-hydroxy-cis-decalin]
$^1$H-NMR δ: 6.4 (d, 1H), 6.1 (dd, 1H), 8 (dd, 1H), 2.4–1.1 (m, 17H)

MS m/e: 225 (M$^+$)

EXAMPLE 3

A mixed solution containing 1 mmol of 4a,9a-dihydroxy-cis-syn-cis-perhydroanthracene, 0.1 mmol of di(η$^5$-pentamethylcyclopentadienyl)samariumditetrahydrofuran [CP$^+_2$Sm(THF)$_2$], and 2.2 mmol of vinyl acrylate in 2 ml of dioxane was stirred at 50° C. for 6 hours. A gas chromatographic analysis of a reaction mixture reveled that 4a,9a-bisacryloyloxy-cis-syn-cis-perhydroanthracene of the following formula was formed in a yield of 72%.

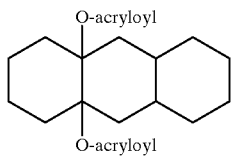

[Spectrum Data of 4a,9a-Bisacryloyloxy-cis-syn-cis-perhydroanthracene]

IR (cm$^{-1}$): 2990, 1705, 1260

MS m/e: 333 (M$^+$)

EXAMPLE 4

The procedure of Example 3 was repeated, except that the amount of vinyl acrylate was changed to 1 mol, and 4 a-acryloyloxy-9a-hydroxy-cis-syn-cis-perhydroanthracene of the following formula was formed in a yield of 41%.

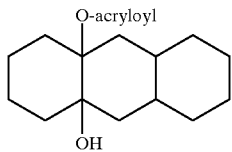

[Spectrum Data of 4a-Acryloyloxy-9a-hydroxy-cis-syn-cis-perhydroanthracene]

IR (cm$^{-1}$): 3500–3100 (br, OH), 2980, 1690, 1250

MS m/e: 279 (M$^+$)

EXAMPLE 5

A mixed solution containing 1 mmol of 2-hydroxyexotricyclo[5.2.1.0$^{2,6}$]decane, 0.1 mmol of sarmarium(III) triflate, and 4.5 mmol of isopropenyl acrylate in 2 ml of dioxane was stirred at 50° C. for 6 hours. A gas chromatographic analysis of a reaction mixture revealed that 2-acryloyloxyexotricyclo[5.2.1.0$^{2,6}$]decane of the following formula was formed in a yield of 82%.

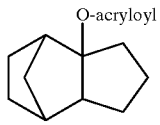

[Spectrum Data of 2-Acryloyloxyexotricyclo[5.2.1.0$^{2,6}$]decane]

IR (cm$^{-1}$): 2950, 1750, 1240

MS m/e: 207 (M$^+$)

EXAMPLE 6

A mixed solution containing 1 mmol of 2,6-dihydroxyexotricyclo[5.2.1.0$^{2,6}$]decane, 0.1 mmol of scandium(III) triflate, and 2.2 mmol of isopropenyl acrylate in 2 ml of dioxane was stirred at 50° C. for 6 hours. A gas chromatocraphic analysis of a reaction mixture revealed that 2,6-bisacryloyloxyexotricyclo[5.2.1.0$^{2,6}$]decane of the following formula was formed in a yield of 75%.

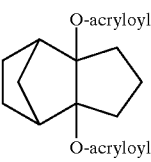

[Spectrum Data of 2,6-Bisacryloyloxyexotricyclo[5.2.1.0$^{2,6}$]decane]

IR (cm$^{-1}$): 2960, 1740, 1230

MS m/e: 277 (M$^+$)

EXAMPLE 7

The procedure of Example 6 was repeated, except that the amount of isopropenyl acrylate was changed to 1 mmol. As a result, 2-acryloyloxy-6-hydroxyexotricyclo[5.2.1.0$^{2,6}$]decane of the following formula was formed in a yield of 56%.

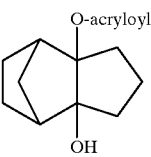

[Spectrum Data of 2-Acryloyloxy-6-hydroxyexotricyclo[5.2.1.0$^{2,6}$]decane]

IR (cm$^{-1}$): 3300, 2990, 1730, 1250

MS m/e: 223 (M$^+$)

EXAMPLE 8

A mixed solution containing 1 mmol of 2,5-dihydroxyexotricyclo[5.2.1.0$^{2,6}$]decane, 0.1 mmol of samarium chloride (SmI$_2$), and 2.2 mmol of isopropenyl acrylate in 2 ml of dioxane was stirred at 50° C. for 6 hours. A gas chromatographic analysis of a reaction mixture revealed that 2,5-bisacryloyloxyexotricyclo[5.2.1.0$^{2,6}$]decane of the following formula was formed in a yield of 85%.

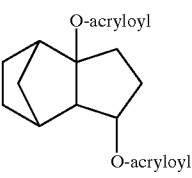

[Spectrum Data of 2,5-Bisacryloyloxyexotricyclo[5.2.1.0$^{2,6}$]decane]

IR (cm$^{-1}$): 2900, 1740, 1200

MS m/e: 277 (M$^+$)

What is claimed is:

1. A polymerizable alicyclic ester shown by the following formula (1) or (2):

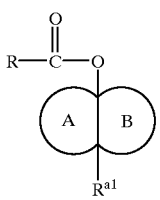

(1)

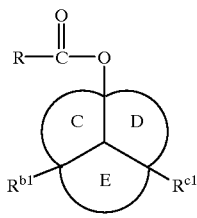

(2)

wherein each of ring A, ring B, ring C, ring D, and ring E is a non-aromatic carbon ring, R is a polymerizable unsaturated group, and each of $R^{a1}$, $R^{b1}$ and $R^{c1}$ is, identical to or different from one another, a hydrogen atom, a hydroxyl group which may be protected by a protective group, or an $RCO_2$ group, where R has the same meaning as defined above.

2. A polymerizable alicyclic ester according to claim 1, wherein each of the ring A, the ring B, the ring C, the ring D, and the ring E is a cyclopentane ring, a cyclohexane ring or a bridged ring.

3. A polymerizable alicyclic ester according to claim 1, wherein a polycyclic carbon ring formed by the ring A and the ring B, or by the ring C, the ring D and the ring E in the formula (1) or in the formula (2) is a perhydroindene ring, a decalin ring, a perhydrofluorene ring, a perhydroanthracene ring, perhydrophenanthrene ring, a tricyclo[5.2.1.0$^{2,6}$]decane ring, a perhydroacenaphthene ring, or a perhydrophenalene ring.

4. A polymerizable alicyclic ester according to one of claims 1 to 3, wherein R is a vinyl group, an isopropenyl group, or an allyl group.

5. A process for producing a polymerizable alicyclic ester, said process comprising the step of allowing an alicyclic alcohol shown by the following formula (3) or (4):

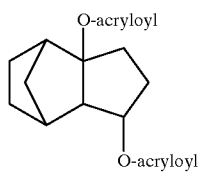

wherein each of ring A, ring B, ring C, ring D and ring E is a non-aromatic carbon ring, and each of $R^{a2}$, $R^{b2}$, and $R^{c2}$ is, identical to or different from one another, a hydrogen atom or a hydroxyl group which may be protected by a protective group, to react with an unsaturated carboxylic acid shown by the following formula (5):

$$RCO_2H \qquad (5)$$

wherein R is a polymerizable unsaturated group, or a reactive derivative thereof in the presence of a catalyst composed of a compound of Group 3 element of the Periodic Table of Elements to yield an ester shown by the following formula (1) or (2):

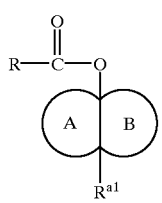

(1)

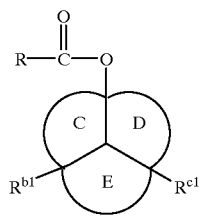

(2)

wherein each of $R^{a1}$, $R^{b1}$ and $R^{c1}$ is, identical to or different from one another, a hydrogen atom, a hydroxyl group which may be protected by a protective group, or an $RCO_2$ group, wherein R has the same meaning as defined above; and the ring A, ring B, ring C, ring D, ring E, and R have the same meanings as defined above.

6. A process for producing a polymerizable alicyclic ester according to claim 5, wherein said compound of Group 3 element of the Periodic Table of Elements is a rare earth compound.

* * * * *